United States Patent [19]

Szabadkai et al.

[11] Patent Number: 4,937,252
[45] Date of Patent: Jun. 26, 1990

[54] 2-THIAZOLIDINONE DERIVATIVES, PHARMACEUTICAL COMPOSITIONS CONTAINING THEM AND PROCESS FOR PREPARING SAME

[75] Inventors: István Szabadkai; Kálmán Harsányi, both of Budapest; Ágnes Lampert, Ajka; György Domány, Budapest; Béla Hegedüs, Budapest; Márta K. Pap, Budapest; Elemér Ezer, Budapest; Judit Matuz, Budapest; Katalin Sághy, Budapest; László Szporny, Budapest; György Hajós, Budapest; Kristztina Székely, Budapest, all of Hungary

[73] Assignee: Richter Gedeon Vegyeszeti Gyar Rt., Budapest, Hungary

[21] Appl. No.: 283,809

[22] Filed: Dec. 13, 1988

[30] Foreign Application Priority Data

Dec. 14, 1987 [HU] Hungary .................. 5632/87

[51] Int. Cl.$^5$ .................. C07D 277/14; A01K 31/425
[52] U.S. Cl. ................................. 514/369; 548/182
[58] Field of Search .................. 548/182; 514/364

[56] References Cited

U.S. PATENT DOCUMENTS 3,066,919 10/1961 Gaul .................. 548/182

FOREIGN PATENT DOCUMENTS 200415 12/1986 European Pat. Off. ............ 548/182
0127466 11/1978 Japan .................. 548/182

OTHER PUBLICATIONS

Clark, J. Chem. Soc. (8), 103 (1971).
Gaul, J. Org. Chem., 26 5103 (1961).

Primary Examiner—Robert Gerstl
Attorney, Agent, or Firm—Keil & Weinkauf

[57] ABSTRACT

The present invention relates to novel 2-thiazolidinone derivatives of the general formula (I),

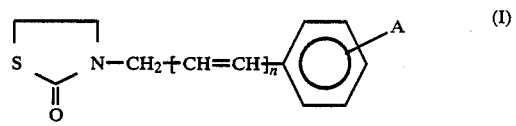

wherein
A stands for hydrogen, halogen or a $C_{1-4}$alkyl, $C_{1-4}$alkoxy or nitro group; and
n is 0 or 1.

The compounds according to the invention show a cytoprotective and gastric acid secretion-inhibiting effect and thus, may be used in the therapy of gastric and duodenal ulcers.

6 Claims, No Drawings

2-THIAZOLIDINONE DERIVATIVES, PHARMACEUTICAL COMPOSITIONS CONTAINING THEM AND PROCESS FOR PREPARING SAME

This invention relates to novel 2-thiazolidinone derivatives of the general formula (I),

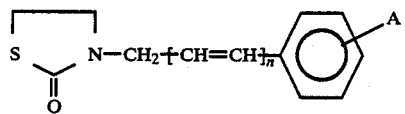

wherein
A stands for hydrogen, halogen or a $C_{1-4}$alkyl, $C_{1-4}$-alkoxy or nitro group; and
n is 0 or 1
as well as the pharmaceutical compositions containing these compounds.

The therapeutical importance of the novel compounds of general formula (I) is very high since the number of patients suffering from gastric and duodenal ulcers is continuously increasing both in the absolute as well as in the relative sense. Although a number of antiulcer drugs are available, a similar effect of only 2-(3,4-dimethoxyphenyl)-5-methyl-4-thiazolidinone (KM-1146) having a significantly different structure from the compounds of general formula (I) has been described within the substance class of the thiazolidines [Arzneim.-Forsch./Drug Res. 36/II/8, 1236 (1986)].

Among the compounds of the general formula (I), 3-(4-nitrophenylmethyl)-2-thiazolidinone has only been reported in the literature, which is the product of the alkaline hydrolysis of 2-(4-nitrophenylmethylthio)-3-(4-nitrophenylmethyl)-2-thiazolinium bromide [J. Chem. Soc. 1971, 103). However, the melting point (137°–138° C.) given in the cited paper significantly differs from that of the product prepared by us in an other way (see Example 6: i.e. 146°–148° C.). The structure of 3-phenylmethyl-2-thiazolidinone was given as a supposed but not isolated intermediate in the oxidation of 3-phenylmethyl-2-thiazolidinethione to 3-phenylmethyl-2-thiazolidine-1,1-dioxide [J. Org. Chem. 25, 5103 (1961)].

According to an other aspect of the invention, there is provided a process for the preparation of the new compounds of the general formula (I), wherein
A stands for hydrogen, halogen or a $C_{1-4}$alkyl, $C_{1-4}$-alkoxy or nitro group; and
n is 0 or 1,
which comprises
(a) reacting a cysteamine derivative of the general formula (II),

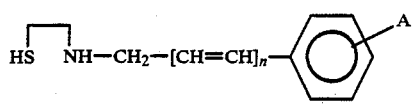

wherein A and n are as defined above, with a carbonic acid derivative of the general formula (III),

wherein Y means halogen, amino, phenoxy or pyridyloxy group; or
(b) subjecting a compound of the general formula

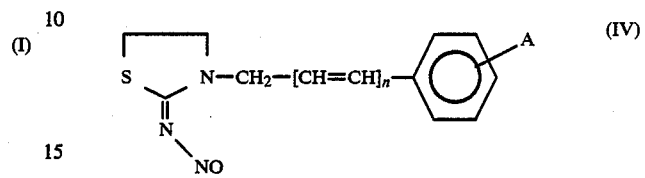

wherein A and n are as defined above, to a thermal decomposition; or
(c) reacting a compound of the general formula (V),

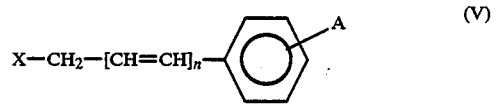

wherein A and n are as defined above and X stands for halogen, mesyloxy or tosyloxy group, with 2-thiazolidinone.

The reaction according to process (a) of the invention is carried out in the presence of a solvent. Depending on the reactivity of the reactants used, suitable solvents are $C_{1-5}$ alcohols, $C_{3-8}$ ketones, nitriles, aromatic or chlorinated hydrocarbons. It is usually suitable to accomplish the reaction at a temperature between 40° C. and 130° C., optionally at the boiling point of the solvent used. The side products of the reaction depends on the nature of the leaving group. Hydrogen chloride or ammonia (when $Y=NH_2$) formed in the reaction partly evolve in a gaseous form from the reaction mixture whereas in other cases, phenol or hydroxypyridine formed in the condensation reaction have to be removed by alkaline extraction or distillation after evaporating the reaction mixture. From the reaction mixture thus pretreated, the product may be isolated by distillation, column chromatography or crystallization.

The compounds of the general formula (IV) used as starting substances in process (b) of the invention are prepared by nitrosating the corresponding imino compound or its salt. The compound of the general formula (IV) thus prepared is isolated, dried and subjected without purification to a thermal decomposition by refluxing in a high-boiling solvent (e.g. in a $C_{3-6}$ alcohol, $C_{6-10}$ aromatic hydrocarbon). After evaporation of the solvent, the residue is rubbed with a suitable solvent and the product is separated by filtration.

The reaction according to process (c) of the invention is carried out in the presence of a solvent. $C_{3-8}$ ketones or aqueous ketones, dimethylformamide, dimethylsulfoxide, preferably methyl isobutyl ketone may be used in the presence of an acid binding agent, preferably by using an alkaline metal carbonate or hydrogen carbonate for this purpose. After filtering off the inorganic precipitate and removing the solvent, the product is purified by distillation, crystallisation or column chromatography. The preparation of 2-thiazolidinone used as starting substance is known from the literature [J.

Am. Chem. Soc. 73, 5349 (1956); J. Chem. Soc. 1952, 3094].

The cysteamine derivatives of the general formula (II) employed as starting compounds may be prepared by the complex metal hydride reduction of 2-arylthiazoline derivatives which in turn are obtained by reacting cysteamine with the appropriate oxo compounds [J. Org. Chem. 27, 4712 (1963). The 2-aminothiazolidine derivatives of the general formula (IV) can be prepared by alkylation of the corresponding 2-amino-2-thiazoline derivatives [see e.g.: Zhurnal Obsch. Chim. 1962, 3215).

Based on the pharmacological investigations, 3-phenylmethyl-2-thiazolidinone (code name: RGH-6148) is an outstanding member of the compounds of general formula (I).

Pharmacology (1) RGH-6148 has antisecretory effect in pylorus ligated (Shay-rat) rats. [Gastroenterology 5, 43 (1945)]$ED_{50}$: 2.6 mg/kg p.o. and 3.7 mg/kg i.p.. This compound does not inhibit the stimulated (by histamne, charbachole, pentagastrine) acid secretion in perfused rat stomach.

(2) Pretreatment with RGH-6148 shows cytoprotective (gastroprotective) effect against acidified-ethanol induced gastric damage: $ED_{50}=6$ mg/kg p.o. [Gastroenterology 77, (1979)]

(3) RGH-6148 prevents the gastric ulcer produced by
  (a) indomethacin: $ED_{50}=1.0$ mg/kg p.o.
  (b) aspirin: $ED_{50}=1.3$ mg/kg p.o.
  (c) aspirin+stress $ED_{50}=22.0$ mg/kg p.o.

(4) RGH-6148 accelerates the healing of chronic gastric ulcer in rats produced by acetic-acid at 3 mg/kg/daily with 38%.

(5) RGH-6148 inhibits the indomethacin-induced intestinal ulcer.

(6) Acut $LD_{50}$ of RGH-6148 700 mg/kg p.o. in rat.

Implications

Together with some of literature findings, our present results suggest a working hypothesis for the pathomechanism of gastric ulcer and for the mechanism of action of RGH-6148.

These hypotheses emphasized the role of mucosal mast cell. The fact that RGH-6148 does not inhibit the stimulated acid secretion suggests that the place of action might be as well on the level of mucosal mast cells, and not on the parietal cells one.

RGH-6148 represents a new class of antiulcer drugs, which can be called as a mucosal mast cell protector (MMCP).

3-(2-Nitrophenylmethyl)-2-thiazolidinone, when orally administered in a dose of 10 mg/kg, resulted in 100% inhibition in the cytoprotective test (Robert test) in comparison to the control; and, when orally administered in a dose of 25 mg/kg, it induced 60% inhibition in the acid secretion-inhibiting test (Shay test) in comparison to the control. When tested by using the same method, 3-(4-chlorophenylmethyl)-2-thiazolidinone showed an inhibition of 30% and 60%, respectively.

The invention is illustrated in detail by the following non-limiting Examples.

EXAMPLE 1

Preparation of 3-phenylmethyl-2-thiazolidinone (a) A solution containing 33.6 g (0.2 mol) of N-phenylmethylcysteamine and 42.8 g (0.2 mol) of diphenyl carbonate in 200 ml of ethanol is refluxed under nitrogen for 24 hours, then ethanol is evaporated under reduced pressure. The residue is taken up in ethyl acetate, washed with 2N sodium hydroxide solution until it becomes free of phenol, then washed with water, dried and evaporated. The residue is distilled under reduced pressure to give 21.8 g (56.4%) of the title compound, b.p.: 140° C./1.5 Hgmm, which solidifies under petroleum ether, m.p.: 50°–51° C.

Analysis: calculated for $C_{10}H_{11}NOS$ (molecular weight 193.26): C 62.15; H 5.73; N 7,25; S 16.59%; found: C 62.23; H 5.98; N 7,17; S 16.45.

IR (KBr): 1660 cm$^{-1}$ (C=O); 1445 cm$^{-1}$ (N—CH$_2$); 1230 cm$^{-1}$ (S—CH$_2$).

$^1$H-NMR (CDCl$_3$): 3.0–3.7 ppm (m, 4H, 2 CH$_2$); 4.5 ppm (s, 2H, CH$_2$); 7.3 ppm (s, 5H, ArH).

(b) After saturating 30 ml of toluene with phosgene at 10° C., a solution of 10.02 g (0.06 mol) of N-phenylmethylcysteamine in 15 ml of toluene is added dropwise. A white, thick precipitate appears. The mixture is slowly heated to the boiling point and refluxed until a clear solution is obtained. The hot solution is bubbled through with nitrogen until it becomes free from phosgene and then evaporated under reduced pressure.

The residue is refluxed in 40 ml of ethanol for 2 hours, then ethanol is evaporated under reduced pressure and the residue is distilled under reduced pressure. The distillate solidifies under petroleum ether. Thus, 6.65 g (57.3%) of the title compound are obtained, m.p.: 50°–51° C.

(c) To a solution of 2.73 g (0.01 mol) of 2-imino-3-phenylmethylthiazolidine hydrobromide in 10 ml of water 1.36 g of anhydrous sodium acetate and 0.62 ml of glacial acetic acid are added, then 0.75 g of sodium nitrite dissolved in 3 ml of water is dropped to the above mixture at 5° C. under stirring, then the mixture is stirred at 5° C. for additional 3 hours. After standing in a refrigerator overnight, the solution is stirred at room temperature for 3 hours. After rubbing, a precipitate appears which is filtered off, washed with water, dried and then refluxed with five volumes of n-butanol for 2 hours. After evaporating the solvent, the residue is thoroughly rubbed with diisopropyl ether and the product is filtered off. Thus, 0,81 g (42.3%) of the title product is obtained, m.p.: 49°–50° C.

(d) A mixture containing 3.09 g (0.03 mol) of 2-thiazolidinone, 11.2 g of potassium carbonate, 1.8 g of potassium hydrogen carbonate, 0.5 ml of water, 30 ml of methyl isobutyl ketone and 3.0 ml (0.033 mol) of benzyl bromide is refluxed for 7 hours. After cooling down, the reaction mixture is washed twice with 30 ml of water each, the organic phase is dried and evaporated. The yellow oily product (which solidifies on standing) may be purified by column chromatography (by using Kieselgel 60 of 230–400 mesh as sorbent and chloroform as eluent) to give 3.2 g (55.2%) of the title compound, m.p.: 50°–51° C.

EXAMPLE 2

Preparation of 3-(4-methoxyphenylmethyl)-2-thiazolidinone

A solution containing 4.53 g (0.025 mol) of N-(4-methoxyphenylmethyl)-cysteamine and 5.35 g (0.025 mol) of diphenyl carbonate in 25 ml of ethanol is refluxed under nitrogen for 24 hours, then evaporated. The residue is taken up in ethyl acetate, washed with 2N sodium hydroxide solution until it becomes free from phenol, then washed with water, dried and evaporated.

The residue becomes solid under ether. Thus, 1.82 g (32.6%) of the title compound are obtained, m.p.: 84°–86° C.

Analysis: calculated for $C_{11}H_{13}NO_2S$ (molecular weight 223.29): C 59.17; H 5.87; N 6.27; S 14.36%; found: C 59.35; H 5.91; N 6.03; S 14.23.

IR (KBr): 1640 cm$^{-1}$ (C=O): 2850 cm$^{-1}$ (O—CH$_3$); 1247 cm$^{-1}$ (Ar—O—C).

$^1$H-NMR (CDCl$_3$): 3.3 ppm (m, 4H, 2 CH$_2$); 3.8 ppm (s, 3H, CH$_3$); 4.4 ppm (s, 2H, CH$_2$); 7.0 ppm (q, 4H, ArH).

EXAMPLE 3

Preparation of 3-(2-chlorophenylmethyl)-2-thiazolidinone

The procedure of Example 2 is followed 5.05 g (0.025 mol) of N-(2-chlorophenylmethyl)cysteamine are reacted with 5.35 g (0.025 mol) of diphenyl carbonate and then worked up. The product is purified by column chromatography (by using Kieselgel 60 of 230–400 mesh as sorbent and chloroform as eluent) to obtain 2.5 g (43.9%) of the title compound, $n_D^{30}$=1.600.

Analysis: calculated for $C_{10}H_{10}ClNOS$ (molecular weight 227.71): C 52.75; H 4.43; N 6.15; S 14.07%; found: C 52.98; H 4.25; N 6.28; S 14.22.

IR (KBr): 1670 cm$^{-1}$ (C=O); 1055 cm$^{-1}$ (Ar—Cl).

$^1$H-NMR (CDCl$_3$): 3.3 ppm (m, 2H, CH$_2$); 3.6 ppm (m, 2H, CH$_2$); 4.7 ppm (s, 2H, CH$_2$); 7.4 ppm (s, 5H, ArH).

EXAMPLE 4

Preparation of 3-(4-methylphenylmethyl)-2-thiazolidinone

The procedure of Example 2 is followed, 4.0 g (0.022 mol) of N-(4-methylphenylmethyl)cysteamine are reacted with 4.71 g (0.022 mol) of diphenyl carbonate then the reaction mixture is worked up to give 1.36 g (29.8%) of the title compound, m.p.: 49°–50° C.

Analysis: calculated for $C_{11}H_{13}NOS$ (molecular weight 207.29): C 63.73; H 6.32; N 6.76; S 15.47%; found: C 63.78; H 6.39; N 6.67; S 15.44.

IR (KBr): 1660 cm$^{-1}$ (C=O).

$^1$H-NMR (CDCl$_3$): 2.2 ppm (s, 3H, CH$_3$); 2.9–3.6 ppm (m, 4H, 2 CH$_2$); 4.3 ppm (s, 2H, CH$_2$); 7.0 ppm (s, 5H, ArH).

EXAMPLE 5

Preparation of 3-(2-nitrophenylmethyl)-2-thiazolidinone

A mixture containing 3.09 g (0.03 mol) of 2-thiazolidinone, 11.2 g of potassium carbonate, 1.8 g of potassium hydrogen carbonate, 0.5 ml of water, 30 ml of methyl isobutyl ketone and 6.5 g (0.03 mol) of nitrobenzyl bromide is refluxed for 6 hours, then cooled down and thoroughly mixed with 50 ml of water. The mixture is filtered and the clear filtrate is separated. The organic phase is washed with 10 ml of water, dried and evaporated. The oily residue is recrystallized from ethanol to give 2.65 g (37.0%) of the title compound, m.p.: 92°–93° C.

Analysis: calculated for $C_{10}H_{10}N_2O_3S$ (molecular weight 238.26): C 50.41; H 4.23; N 11.76; S 13.45%; found: C 50.63; H 4.10; N 11.84; S 13.63.

IR (KBr): 1670 cm$^{-1}$ (C=O); 1525, 1345 cm$^{-1}$ (NO$_2$).

$^1$H-NMR (CDCl$_3$): 3.1–3.8 ppm (m, 4H, 2 CH$_2$); 4.9 ppm (s, 2H, CH$_2$); 7.2–8.3 ppm (m, 4H, ArH).

EXAMPLE 6

Preparation of 3-(4-nitrophenylmethyl)-2-thiazolidinone

The process of Example 5 is followed, except that 4-nitrobenzyl bromide is used instead of 2-nitrobenzyl bromide. Thus, 3.89 g (54.4%) of the title compound are obtained, m.p.: 146°–148° C.

Analysis: calculated for $C_{10}H_{10}N_2O_3S$ (molecular weight 238.26): C 50.41; H 4.23; N 11.76; S 13.45%; found: C 50.65; H 4.34; N 11.65; S 13.57.

IR (KBr): 1658 cm$^{-1}$ (C=O); 1513, 1352 cm$^{-1}$ (NO$_2$).

$^1$H-NMR (DMSO-d$_6$): 3.5 ppm (m, 4H, 2 CH$_2$); 4.6 ppm (s, 2H, CH$_2$); 7.8 ppm (q, 4H, ArH).

EXAMPLE 7

Preparation of 3-(4-chlorophenylmethyl)-2-thiazolidinone

The process of Example 5 is followed, except that 5.0 g (0.03 mol) of 4-chlorobenzyl chloride are used instead of 2-nitrobenzyl bromide. Thus, 3.95 g (56%) of the title compound are obtained, m.p.: 68°–69° C.

Analysis: calculated for $C_{10}H_{10}ClNOS$ (molecular weight 227.71): C 52.75; H 4.43; N 6.15; S 14.07%; found: C 52.83; H 4.67; N 6.12; S 14.24.

IR (KBr): 1670 cm$^{-1}$ (C=O); 1095 cm$^{-1}$ (Ar—Cl).

$^1$H-NMR (CDCl$_3$): 3.3 ppm (q, 2H, CH$_2$); 3.5 ppm (q, 2H, CH$_2$); 4.5 ppm (s, 2H, CH$_2$); 7.3 ppm (s, 4H, ArH).

EXAMPLE 8

Preparation of 3-cinnamyl-2-thiazolidinone

The process of Example 5 is followed, except that 4.58 g (0.03 mol) of cinnamyl chloride are used instead of 2-nitrobenzyl bromide. After purifying by chromatography (by using Kieselgel 60 of 230–400 mesh as sorbent and an 8:2 mixture of ethyl acetate and petroleum ether as eluent) and recrystallisation from diisopropyl ether, 3.92 g (59.6%) of the title product are obtained, m.p.: 50°–52° C.

Analysis: calculated for $C_{12}H_{13}NOS$ (molecular weight 219.30); C 65.72; H 5.97; N 6.39; S 14,62%; C 65,93; H 6.06; N 6.26; S 14.51.

IR (KBr): 1670 cm$^{-1}$ (C=O); 980 cm$^{-1}$ (C=C).

$^1$H-NMR (CDCl$_3$): 3.2 ppm (m, 2H, CH$_2$); 3.6 ppm (m, 2H, CH$_2$); 4.0 ppm (d, 2H, CH$_2$); 5.9–6.6 ppm (m, 2H, 2 CH); 7.3 ppm (s, 5H, ArH).

EXAMPLE 9

Pharmaceutical composition

Preparation of tablets containing 50 mg of active ingredient each

For the preparation of 1000 tablets, the following components are used:
3-Phenylmethyl-2-thiazolidinone: 50 g
Lactose: 200 g
Starch: 32 g
Magnesium stearate: 3 g The active ingredient and the auxiliary materials are mixed in a mixer equipment and then compressed to tablets in a tabletting machine.

We claim:

1. A 2-thiazolidinone derivative of the formula:

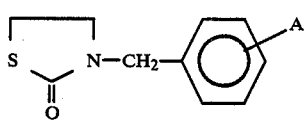

wherein A is hydrogen or halogen.

2. 3-Phenylmethyl-2-thiazolidinone.

3. A pharmaceutical composition for treating gastric and duodenal ulcers which comprises: a pharmaceutically acceptable carrier and an antiulcer effective amount of a 2-thiazolidinone derivative of the formula:

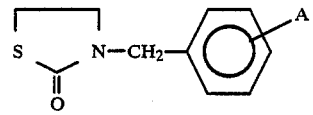

wherein A is hydrogen, halogen or nitro.

4. The pharmaceutical composition of claim 3, wherein the 2-thiazolidinone derivative is 3-phenylmethyl-2-thiazolidinone.

5. A process for treating patients suffering from gastric or duodenal ulcers which comprises: orally administering to said patients and antiulcer effective amount of a composition as described in claim 11.

6. The process of claim 5, wherein the 2-thiazolidinone derivative is 3-phenylmethyl-2-thiazolinone.